(12) United States Patent
Kashanchi et al.

(10) Patent No.: US 6,686,333 B1
(45) Date of Patent: Feb. 3, 2004

(54) INHIBITION OF HIV REPLICATION USING SOLUBLE TAT PEPTIDE ANALOGS

(75) Inventors: Fatah Kashanchi, Montclair, NJ (US); Mohammad Reza Sadaie, Germantown, MD (US); John Brady, Gaithersburg, MD (US)

(73) Assignee: The United States of America as represented by the Department of Health and Human Resources, Washington, DC (US)

( * ) Notice: Subject to any disclaimer, the term of this patent is extended or adjusted under 35 U.S.C. 154(b) by 0 days.

(21) Appl. No.: 09/269,991

(22) PCT Filed: Oct. 2, 1997

(86) PCT No.: PCT/US97/17704

§ 371 (c)(1),
(2), (4) Date: Sep. 7, 1999

(87) PCT Pub. No.: WO98/14587

PCT Pub. Date: Apr. 9, 1998

Related U.S. Application Data

(60) Provisional application No. 60/027,658, filed on Oct. 4, 1996.

(51) Int. Cl.[7] ............... A61K 38/16; C12N 15/49; C07K 14/16
(52) U.S. Cl. ............... 514/14; 514/2; 530/300; 530/327; 435/235.1; 435/320.1; 435/252.3; 435/69.1; 536/23.1; 536/23.7; 424/93.6
(58) Field of Search .............. 514/14, 2; 530/300, 530/327; 435/235.1, 320.1, 252.3, 69.1; 536/23.1, 23.7; 424/93.6

(56) References Cited

FOREIGN PATENT DOCUMENTS

| EP | 0614980 A | * | 9/1994 |
| WO | WO 89/12461 A | * | 12/1989 |
| WO | WO 90/13630 A | * | 11/1990 |

OTHER PUBLICATIONS

Green et al., Cell, vol. 58, No. 1, Jul. 1989, pp. 215–223.*
Frankel et al., Proc. Nat. Acad. Sci. USA, vol. 86, No. 19, Oct., 1989, pp. 7397–7401.*
Pearson et al., Proc. Nat. Acad. Sci. USA, vol. 87, No. 13, Jul., 1990, pp. 5079–5083.*
Yahi et al., J. of Virology, vol. 68, 1994, pp. 5714–5720.*

* cited by examiner

Primary Examiner—Christopher S. F. Low
Assistant Examiner—Chih-Min Kam
(74) Attorney, Agent, or Firm—Townsend & Townsend & Crew LLP

(57) ABSTRACT

Methods and compositions for inhibiting replication of HIV in a mammalian cell. The compositions can be a peptide, or a nucleic acids encoding a peptide, which inhibits transactivation of the HIV long terminal repeat.

8 Claims, No Drawings

```
                          SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
         (A) LENGTH: 14 amino acids
         (B) TYPE: amino acid
         (C) STRANDEDNESS: <Unknown>
         (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /product= "OTHER"
             /note= "Xaa = Leu, Met, Ile, Thr, Gln
             or Val"

(ix) FEATURE:
         (A) NAME/KEY: Modified-site
         (B) LOCATION: 4
         (D) OTHER INFORMATION: /product= "OTHER"
             /note= "Xaa = Thr, Arg, Lys or Asn"

(ix) FEATURE:
         (A) NAME/KEY: Modified-site
         (B) LOCATION: 5
         (D) OTHER INFORMATION: /product= "OTHER"
             /note= "Xaa = any amino acid exclusive
             of Lys"

(ix) FEATURE:
         (A) NAME/KEY: Modified-site
         (B) LOCATION: 11
         (D) OTHER INFORMATION: /product= "OTHER"
             /note= "Xaa = Tyr or His"

(ix) FEATURE:
         (A) NAME/KEY: Modified-site
         (B) LOCATION: 13
         (D) OTHER INFORMATION: /product= "OTHER"
             /note= "Xaa = Arg or Lys"

(xi) SEQUENCE DESCRIPTION: SEQ ID NO: 1:
```

```
Cys Phe Xaa Xaa Xaa Gly Leu Gly Ile Ser Xaa Gly Xaa Lys
1               5                   10
```

(2) INFORMATION FOR SEQ ID NO: 2:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

```
Val Cys Phe Thr Thr Lys Ala Leu Gly Ile Ser Tyr Gly Arg Lys
1               5                   10                  15
```

(2) INFORMATION FOR SEQ ID NO: 3:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

```
Val Cys Phe Thr Thr Ala Ala Leu Gly Ile Ser Tyr Gly Arg Lys
1               5                   10                  15
```

(2) INFORMATION FOR SEQ ID NO: 4:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

```
Val Cys Phe Thr Thr Lys Ala Leu Ser Ile Ser Tyr Gly Arg Lys
1               5                   10                  15
```

(2) INFORMATION FOR SEQ ID NO: 5:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

```
Val Cys Phe Thr Thr Lys Ala Leu Gly Ile Ala Tyr Gly Arg Lys
1               5                   10                  15
```

(2) INFORMATION FOR SEQ ID NO: 6:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

```
Val Cys Phe Thr Thr Lys Ala Leu Gly Ile Ser Ala Gly Arg Lys
1               5                   10                  15
```

(2) INFORMATION FOR SEQ ID NO: 7:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 7:

```
Val Cys Phe Thr Thr Ala Ala Leu Ser Ile Ser Tyr Gly Arg Lys
1               5                   10                  15
```

(2) INFORMATION FOR SEQ ID NO: 8:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 8:

```
Val Cys Phe Thr Thr Ala Ala Leu Gly Ile Ala Tyr Gly Arg Lys
1               5                   10                  15
```

(2) INFORMATION FOR SEQ ID NO: 9:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

```
Val Cys Phe Thr Thr Ala Ala Leu Gly Ile Ser Ala Gly Arg Lys
1               5                   10                  15
```

(2) INFORMATION FOR SEQ ID NO: 10:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 10:

```
Lys Lys Lys Gly Pro Lys Glu Lys Gly Cys
1               5                   10
```

(2) INFORMATION FOR SEQ ID NO: 11:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide

```
        (xi) SEQUENCE DESCRIPTION: SEQ ID NO: 11:

Lys Lys Lys Lys Lys Gly Cys
1               5

(2) INFORMATION FOR SEQ ID NO: 12:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 12:

Arg Pro Arg Arg Pro Arg Arg Pro Arg Arg Pro Arg Arg Pro Arg
1               5                   10                  15

(2) INFORMATION FOR SEQ ID NO: 13:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 13:

Arg Pro Lys Arg Pro Lys Arg Pro Lys Arg Pro Lys Arg Pro Lys
1               5                   10                  15

(2) INFORMATION FOR SEQ ID NO: 14:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 14:

Lys Pro Arg Lys Pro Arg Lys Pro Arg Lys Pro Arg Lys Pro Arg
1               5                   10                  15

(2) INFORMATION FOR SEQ ID NO: 15:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 15:

Gly Pro Gly Arg Ala Phe
1               5

(2) INFORMATION FOR SEQ ID NO: 16:

(i) SEQUENCE CHARACTERISTICS:
            (A) LENGTH: 156 base pairs
            (B) TYPE: nucleic acid
            (C) STRANDEDNESS: single
            (D) TOPOLOGY: linear (ii) MOLECULE TYPE: DNA (genomic)
```

-continued

```
    (ix) FEATURE:
         (A) NAME/KEY: -
         (B) LOCATION: 1..156
         (D) OTHER INFORMATION: /note= "adenovirus VA-1 promoter"

(xi) SEQUENCE DESCRIPTION: SEQ ID NO: 16:

GGGCACTCTT CCGTGGTCTG GTGGATAAAT TCGCAAGGGT ATCATGGCGT GGACGACCGG        60

GGTTCGAACC CCGGATCCGT GATCCATGCG GTTACCGTCC GCCGCCCGTG CGTCGAACC        120

AGGTGTGCGA CGTCAGACAA CGGGGGAGCG CTCCTT                                 156

(2) INFORMATION FOR SEQ ID NO: 17:

(i) SEQUENCE CHARACTERISTICS:
         (A) LENGTH: 199 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: -
         (B) LOCATION: 1..199
         (D) OTHER INFORMATION: /note= "HIV long terminal repeat (LTR)
             promoter"

(xi) SEQUENCE DESCRIPTION: SEQ ID NO: 17:

TCGAGCTTGC TACAAGGGAC TTTCCGCTGG GGACTTTCCA GGGAGGCGTG GCCTGGGCGG        60

GACTGGGGAG TGGCGAGCCC TCAGATGCTG CATATAAGCA GCTGCTTTTT GCCTGTACTG      120

GGTCTCTCTG GTTAGACCAG ATCTGAGCCT GGGAGCTCTC TGGCTAACTA GGGAACCCAC      180

TGCTTAAGCC TCAATAAAG                                                    199
```

INHIBITION OF HIV REPLICATION USING SOLUBLE TAT PEPTIDE ANALOGS

This application is a 371 PCT/US97/17704, filed Oct. 2, 1997, which claims benefit of provisional application 60/02758, filed Oct. 4, 1996.

TECHNICAL FIELD

The present invention relates to nucleic acid and peptide compositions which inhibit HIV replication in a mammalian cell. The present invention further relates to methods of inhibiting HIV replication in a mammalian cell by administering the compositions of the invention.

BACKGROUND OF THE INVENTION

Human immunodeficiency virus type (HIV-1) encodes a potent transactivator, Tat. Subsequent to the integration of viral DNA, a major function of Tat is to transactivate the viral long terminal repeat (LTR) to regulate the production of viral mRNA (Arya SK, et al. (1985), *Science,* 229:69–73; Sadaie MR, et al. (1988), *Science* 239:910–913). Tat's mechanism of action has been implicated to be at both transcription initiation and elongation (Kashanchi F, et al. (1994), *Nature* 367:295–299; Xhou Q, et al. (1995), *EMBO J,* 14:321–328; Chiang C-M, et al. (1995), *Science,* 267:531–536).

The use of transdominant mutants of peptides derived from the 86-amino acid Tat protein has been suggested as a means to inhibit HIV replication in vivo. Since the pharmaceutical utility of transdominant mutants of minimal length is generally desired, attempts have been made to define the elements of Tat which are necessary and sufficient to inhibit Tat function. Such attempts have been discredited or implicated nearly full length regions of the Tat protein.

Tat structure comprises an amino-terminal domain, a cysteine-rich domain, a core region, and a basic domain. The Tat core domain is a stretch of eleven amino acids between the cysteine-rich and basic domain. The core domain is conserved in all HIV isolates. Kashanchi et al. (*Nature,* 367:295–299 (1994)) reported that the lysine at position 41 of the core was critical for transactivation in vivo.

Green et al. reported that Tat peptides spanning amino acids 37–62 (and including the core domain) could act as transactivators (*Cell,* 55:1179–1188 (1988)). Green et al. also reported that peptides 37–62 and 37–72 having substitutions at positions 41, 46, or 47 and 46/47 inhibit Tat transactivation of the HIV LTR in vivo (*Cell,* 58:215–223 (1989)). Further, Green et al. state that they believed that a double substitution of amino acids 41 and 47 in any peptide backbone would be a good antagonist (WO 89/12461; PCT/US89/02404). However, as set forth below, subsequent studies by independent researchers have raised substantial uncertainties regarding the findings and suggestions of Green et al.

Frankel et al. (*Proc. Natl. Acad. Sci. USA,* 86:7397–7401 (1989)) investigated transactivation of an HIV-1 LTR-CAT gene construct using synthetic peptides from the Tat protein. In sharp contrast to the studies of Green et al., Frankel et al. reported that the transactivation activity of Tat residues 37–62 as reported by Green et al. was inconsistent with their findings. To resolve the apparent discrepancy, Frankel et al. synthesized and tested Tat 37–62 and found that the peptide failed to have any detectable activity under four different assay conditions. Moreover, Frankel et al. note that core domains lacking a complete amino-terminal domain failed to exhibit any inhibitory effect at 20 µg/ml and state that it seemed unlikely that these peptides could be used to specifically block Tat function in vivo. Id. at page 7400.

Pearson et al. (*Proc Nat/Acad Sci USA,* 87:5079–5083 (1990)) studied peptides and mutant peptides derived from the Tat protein to determine the essential features of peptides having the inhibitory transdominant phenotype. In agreement with the findings of Frankel et al., Pearson et al. further discount the findings of Green et al., and instead teach that their mutagenesis studies suggest that both an intact amino terminus and cysteine-rich domain are required for the inhibitory transdominant phenotype.

Further contradicting the findings of Green et al., Mehtali and Sorg (Australian Patent No. 52803/93) report that a Tat variant with a lysine to alanine substitution at position 41 (as in the mutants of Greene et al.) gives completely contradictory results to the study of Greene et al Indeed, instead of inhibiting transactivation, the variant of Mehtali and Sorg appeared to act in cooperation with the native Tat protein and increased transactivation 72% over the control level.

Accordingly, the thrust of the prior art is that the inhibitory transdominant phenotype of a core domain peptide requires an intact amino terminus, as well as a cysteine-rich domain. However, what is needed in the art is an inhibitory transdominant soluble Tat peptide of minimal length for in vitro and in vivo applications. The present invention provides these and other advantages.

SUMMARY OF THE INVENTION

In one aspect, the present invention relates to an isolated transdominant soluble Tat peptide. The transdominant soluble Tat peptide comprises a transdominant peptide sequence Cys-Phe-Xaa$_{39}$-Xaa$_{40}$-Xaa$_{41}$-Gly-Leu-Gly-Ile-Ser-Xaa$_{47}$-Gly-Xaa$_{49}$-Lys (SEQ ID NO:1), wherein Xaa$_{39}$ is an amino acid residue selected from the group consisting of: Leu, Met, Ile, Thr, Gln, and Val; Xaa$_{40}$ is an amino acid residue selected from the group consisting of: Thr, Arg, Lys, and Asn; Xaa$_{41}$ is an amino acid residue exclusive of Lys; Xaa$_{47}$ is an amino acid residue selected from the group consisting of: Tyr and His; Xaa$_{49}$ is an amino acid residue selected from the group consisting of: Arg and Lys. The transdominant peptide sequence comprises an amino acid residue substitution at a position selected from the group consisting of: 44, 46, 47, and combinations thereof. Additionally, the transdominant soluble Tat peptide lacks an intact amino-terminal domain or an intact cysteine-rich domain.

In some embodiments, the transdominant peptide sequence comprises a single amino acid residue substitution at position 44. In other embodiments, the transdominant peptide sequence comprises a single amino acid residue substitution at position 46 or 47. Generally, the transdominant soluble Tat peptide is no longer than 25 amino acid residues in length. In preferred embodiments, the amino acid at position 44 is an alanine residue. Typically, the transdominant peptide sequence is substituted only at position 44.

In another aspect, the present invention relates to an isolated nucleic acid sequence encoding a transdominant soluble Tat peptide. The transdominant soluble Tat peptide comprises a transdominant peptide sequence having the sequence Cys-Phe-Xaa$_{39}$-Xaa$_{40}$-Xaa$_{41}$-Gly-Leu-Gly-Ile-Ser-Xaa$_{47}$-Gly-Xaa$_{49}$-Lys (SEQ ID NO:1), wherein Xaa$_{39}$ is an amino acid residue selected from the group consisting of: Leu, Met, Ile, Thr, Gln, and Val; Xaa$_{40}$ is an amino acid residue selected from the group consisting of: Thr, Arg, Lys, and Asn; Xaa$_{41}$ is an amino acid residue exclusive of Lys; Xaa$_{47}$ is an amino acid residue selected from the group consisting of: Tyr and His; $Xaa_{49}$ is an amino acid residue selected from the group consisting of: Arg and Lys. The transdominant peptide sequence comprises an amino acid residue substitution at a position selected from the group consisting of: 44, 46, 47, and combinations thereof. Additionally, the transdominant soluble Tat peptide lacks an intact amino-terminal domain or an intact cysteine-rich domain.

In a further aspect, the present invention is directed to an expression vector. The expression vector comprises a nucleic acid encoding a transdominant soluble Tat peptide comprising a transdominant peptide sequence having the sequence Cys-Phe-$Xaa_{39}$-$Xaa_{40}$-$Xaa_{41}$-Gly-Leu-Gly-Ile-Ser-$Xaa_{47}$-Gly-$Xaa_{49}$-Lys (SEQ ID NO:1), wherein $Xaa_{39}$ is an amino acid residue selected from the group consisting of: Leu, Met, Iie, Thr, Gln, and Val; $Xaa_{40}$ is an amino acid residue selected from the group consisting of: Thr, Arg, Lys, and Asn; $Xaa_{41}$ is an amino acid residue exclusive of Lys; $Xaa_{47}$ is an amino acid residue selected from the group consisting of: Tyr and His; $Xaa_{49}$ is an amino acid residue selected from the group consisting of: Arg and Lys. The transdominant peptide sequence comprises an amino acid residue substitution at a position selected from the group consisting of: 44, 46, 47, and combinations thereof. Additionally, the transdominant soluble Tat peptide lacks an intact amino-terminal domain or an intact cysteine-rich domain.

In an additional aspect, the present invention relates to a method of inhibiting HIV replication in a mammalian cell. The method comprises administering a therapeutically effective amount of a transdominant soluble Tat peptide to a mammalian cell. The Tat peptide comprises a nucleic acid encoding a transdominant peptide sequence having the sequence Cys-Phe-$Xaa_{39}$-$Xaa_{40}$-$Xaa_{41}$-Gly-Leu-Gly-Ile-Ser-$Xaa_{47}$-Gly-$Xaa_{49}$-Lys (SEQ ID NO:1), wherein $Xaa_{39}$ is an amino acid residue selected from the group consisting of: Leu, Met, Ile, Thr, Gin, and Val; $Xaa_{40}$ is an amino acid residue selected from the group consisting of: Thr, Arg, Lys, and Asn; $Xaa_{41}$, is an amino acid residue exclusive of Lys; $Xaa_{47}$ is an amino acid residue selected from the group consisting of: Tyr and His; $Xaa_{49}$ is an amino acid residue selected from the group consisting of: Arg and Lys. The transdominant peptide sequence comprises an amino acid residue substitution at a position selected from the group consisting of: 44, 46, 47, and combinations thereof. Additionally, the transdominant soluble Tat peptide lacks an intact amino-terminal domain or an intact cysteine-rich domain.

In some embodiments, the transdominant peptide sequence comprises a single amino acid residue substitution at position 44. In other embodiments, the transdominant peptide sequence comprises a single amino acid residue substitution at position 46 or 47. Generally, the transdominant soluble Tat peptide is no longer than 25 amino acid residues in length. In preferred embodiments, the amino acid at position 44 is an alanine residue. Typically, the transdominant peptide sequence is substituted only at position 44. In some embodiments, the therapeutically effective dose is administered ex vivo, in others the therapeutically effective dose is administered in vivo. Preferably, the mammalian cell is a human cell. In some embodiments, administration of the therapeutically effective dose of the transdominant soluble Tat peptide comprises expressing in the cell an isolated nucleic acid encoding the soluble transdominant Tat peptide. In other embodiments, the transdominant soluble Tat peptide is itself administered. Compositions and methods of the present invention have utility as therapeutic or prophylactic agent in inhibiting HIV replication. Various embodiments of this and other aspects of the invention can be had by reference to the specification as a whole.

DETAILED DESCRIPTION OF THE INVENTION

The present invention provides compositions and methods for inhibiting replication of HIV in vivo. Quite unexpectedly, it has been found that soluble Tat peptides having a core domain, but lacking the amino-terminal domain and/or cysteine-rich domain have the inhibitory transdominant phenotype when substitutions are made at positions 41, and 44, 46, or 47. Thus, contrary to the weight of opinion, core domain peptides lacking either the amino-terminal domain and/or cysteine rich domain can be altered to yield peptides with the transdominant phenotype. These soluble Tat peptides have pharmaceutical utility as a means to control replication of HIV in vivo or ex vivo. The soluble Tat peptides also have utility in regulating translation of cloned mRNA comprising a TAR sequence. Thus, the peptide can be used to control synthesis of desired proteins in eukaryotic expression systems.

Definitions

Units, prefixes, and symbols can be denoted in their SI accepted form. Amino acids are referred to herein by either their commonly known three letter symbols or by the one-letter symbols recommended by the IUPAC-IUB Biochemical Nomenclature Commission. Unless otherwise indicated, amino acid sequences are written left to right from amino terminal to carboxyl terminal orientation, respectively. Numeric ranges are inclusive of the numbers defining the range. The headings provided herein are not limitations to the various aspects or embodiments of the invention which can be had by reference to the specification as a whole. Accordingly, the terms defined immediately below are more fully defined by reference to the specification as a whole.

"Transdominant soluble Tat peptide" includes reference to a peptide of less than 300 amino acids in length which comprises a transdominant peptide sequence. The transdominant soluble Tat peptide inhibits tat-induced gene expression from the human immunodeficiency virus long terminal repeat. Inhibition as measured by transfection and chloramphenicol acetyl transferase (CAT) assay according to the method of Example 1, inhibits activation by the Tat protein at least 20%, typically at least 30%, preferably at least 40% or 50%, more preferably at least 60% or 70%, and most preferably at least 80% or 90%, relative to the wild-type Tat protein.

"Transdominant peptide sequence" or "transdominant Tat peptide sequence" includes reference to a contiguous sequence derived from the Tat protein of HIV-1. See, e.g., Pearson et al., *Proc. Natl. Acad. Sci. USA,* 87:5079–5083 (1990); Frankel et al., *Proc. Natl. Acad.Sci. USA* 86:7397–7401 (1989), and the HIV Sequence Database, T-10, MS K710, (Los Alamos, New Mexico 87545), each of which is incorporated herein by reference. The transdominant peptide sequence comprises at least the contiguous amino acids from residue 37 through 50 substituted as provided herein.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The term "amino acid residue exclusive of Lys" includes reference to all amino acids with the exception of lysine or an analog thereof. Typically, any of the other 19 natural amino acids can be substituted for lysine.

The term "nucleic acid" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

As used herein "encoding" or "encoded", with respect to a specified nucleic acid, includes reference to the inclusion of the information for translation into the specified protein. The information is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum* (*Proc. Natl. Acad. Sci.*, 82:2306–2309 (1985), or the ciliate Macronucleus, can be used when the nucleic acid is expressed using these organisms.

The term "expression vector" includes reference to a nucleic acid construct, generated recombinantly or synthetically, with a series of specified nucleic acid elements which permit transcription of a particular nucleic acid in a host cell. The expression vector can be part of a plasmid, virus, or nucleic acid fragment. Typically, the expression vector includes a nucleic acid to be transcribed, and a promoter (e.g., adenovirus VA-1 promoter).

The terms "effective amount" or "amount effective to" or "therapeutically effective amount" includes reference to a dosage sufficient to produce a desired result, such as inhibition of HIV-1 or HIV-2 replication.

By "ex vivo" includes reference to introducing a composition into a cell which is outside the body of the organism from which a cell or cells is obtained or from which a cell line is isolated. Ex vivo transfection is preferably followed by re-infusion of the cells back into the organism. In contrast, "in vivo" includes reference to introducing a composition into a cell which is within the body of the organism from which the cell was obtained or from which a cell line is isolated.

The term "intact amino-terminal domain" includes reference to an amino acid sequence which, when fused to the amino terminus of a HIV-1 Tat protein lacking the amino-terminal domain (e.g., amino acid residues 1–21), is able to cause transactivation of the HIV-1 LTR of at least 20%, generally at least 50%, preferably at least 70%, more preferably at least 80%, and most preferably at least 90% of the wild-type Tat protein transactivation level. Transactivation of the HIV-1 LTR is conveniently assessed using a CAT assay as described herein in Example 1, and e.g., Kashanchi et al., *J. Virol.*, 68(5):3298–3307 (1994); Pearson et al., *Proc. Natl. Acad. Sci. USA*, 87:5079–5083 (1990); Frankel et al, *Proc. Natl. Acad. Sci. USA* 86:7397–7401 (1989), each of which is incorporated herein by reference. Jurkat cells (ATCC CRL-8163) are conveniently employed in transactivation assays.

Methods for constructing fusion proteins are known in the art. See, e.g., Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel).

The term "intact cysteine-rich domain" includes reference to an amino acid sequence which, when fused into a deleted cysteine-rich domain (e.g., amino acid residues 21–37) of a HIV-1 Tat protein, is able to cause transactivation of the HIV-1 LTR of at least 20%, generally at least 50%, preferably at least 70%, more preferably at least 80%, and most preferably at least 90% of the wild-type Tat protein transactivation level.

The terms "isolated" or "biologically pure" include reference to material which is substantially or essentially free from components which normally accompany or interact with it as found in its naturally occurring environment. The isolated material optionally comprises material not found with the material in its natural environment.

The term "operably linked" refers to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Transdominant Soluble Tat Peptides

Transdominant soluble Tat peptides of the present invention are N amino acid residues in length, where N is any of the integers selected from the group consisting of from 12 to 300. Generally, transdominant soluble Tat peptides are less than 300 amino acids in length, typically less than 200 amino acids in length, preferably less than 100 or 50 amino acids in length, more preferably less than 40, 30, or 25 amino acids in length, and most preferably less than 20 amino acids but at least 14 amino acids in length. The transdominant soluble Tat peptide comprises a transdominant Tat peptide sequence.

The transdominant Tat peptide sequence includes the sequence: Cys-Phe-Xaa$_{39}$-Xaa$_{40}$-Xaa$_{41}$-Gly-Leu-Gly-Ile-Ser-Xaa$_{47}$-Gly-Xaa$_{49}$-Lys (SEQ ID NO:1). In the transdominant Tat peptide sequence Xaa$_{39}$ is an amino acid residue selected from the group consisting of: Leu, Met, Ile, Thr, Gln, and Val; Xaa$_{40}$ is an amino acid residue selected from the group consisting of: Thr, Arg, Lys, and Asn; Xaa$_{41}$ is an amino acid residue exclusive of Lys; Xaa$_{47}$ is an amino acid residue selected from the group consisting of: Tyr and His; Xaa$_{49}$ is an amino acid residue selected from the group consisting of: Arg and Lys. Numbering of the amino acids is per the numbering of the HIV-1 Tat protein as disclosed in Pearson et al, *Proc. Natl. Acad. Sci. USA*, 87:5079–5083 (1990); Frankel et al., *Proc. Natl. Acad.Sci. USA* 86:7397–7401 (1989), both of which are incorporated herein by reference, where the amino terminal methionine is numbered as position 1 and the carboxyl terminal residue is position 86. Thus, the transdominant peptide sequence extending from cysteine to lysine, supra, extends from amino acid residue 37 through 50. The sequences of HIV-1 Tat protein variants and the consensus sequences of subtypes of the HIV-1 Tat protein can be had by reference to the HIV Sequence Database, T-10, MS K710, (Los Alamos, N.Mex. 87545), incorporated herein by reference.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and 6) Phenylalanine (F), Tyrosine (Y), Tryptophan (W).

See also, Creighton (1984) Proteins W.H. Freeman and Company.

In preferred embodiments, the amino acid residue at position 41 is not a conservative substitution for lysine. In particularly preferred embodiments, the amino acid residue at position 41 is an alanine. In other embodiments, the transdominant peptide sequence comprises an amino acid residue at the amino terminal and preceding amino acid residue 37 (i.e., at position 36), wherein amino acid residue 36 is selected from the group consisting of: Leu, Val, Ala, Asn, Met, Trp, and Tyr.

The transdominant peptide sequence comprises an amino acid residue substitution at a position selected from the group consisting of: 44, 46, 47, and combinations thereof. The amino acid residue substituted at positions 44, 46, or 47 can be selected from any amino acid other than the one specified in the wild-type Tat sequence for that position. Thus, any of the natural amino acids or analogs thereof which differ from the amino acid residues present at position 44 (Gly), 46 (Ser), or 47 (Tyr or His) can be substituted therefor. In preferred embodiments, the substitution is at position 44. In particularly preferred embodiments, the substitution at position 44 is a serine; the substitution at position 46 or 47 is an alanine.

The amino acids referred to herein are described by shorthand designations as follows:

TABLE I

Amino Acid Nomenclature

| Name | 3-letter | 1 letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | w |
| Tyrosine | Tyr | Y |
| Valine | Val | V |

Generally, the transdominant peptide sequence will be less than 35 amino acid residues in length, typically less than 30, preferably less than 25, and most preferably less than 20 amino acid residues in length.

Those of skill in the art will readily understand that the amino acid sequence which makes up the transdominant soluble Tat peptide and which is linked to the transdominant peptide sequence (i.e., the "non-transdominant peptide sequence") will be incapable of transactivating the HIV LTR (long terminal repeat). By "incapable of transactivating the HIV LTR" is meant that the non-transdominant peptide sequence component of the transdominant soluble Tat peptide will not increase transactivation by more than 20% relative to a control lacking the non-transdominant peptide sequence. Furthermore, the non-transdominant peptide sequence generally should not substantially interfere in the transdominant phenotype provided by the transdominant peptide sequence. Thus, for example, specific or non-specific binding to cellular components to a degree which prevents functioning of the transdominant peptide sequence should be avoided. Usually, the non-transdominant peptide sequence should not substantially reduce cell viability (e.g., increase cell doubling time by more than 10%). Preferably, the transdominant soluble Tat peptide is soluble in an aqueous solution.

Within any of the up to 70 amino acid residues contiguous and extending toward the amino terminal end from amino acid residue 37 of the transdominant peptide sequence, an intact amino-terminal domain and/or an intact cysteine-rich domain is lacking, with one proviso. The proviso is that an amino-terminal domain is directly adjacent and at the amino-terminal end of the cysteine-rich domain. Thus, a construct in which the amino-terminal domain and the cysteine-rich domain are situated so they no longer function to transactivate an HIV LTR when fused to, for example, a Tat protein sequence from 37 through 86, is within the scope of the present invention.

Typically, the transdominant peptide sequence lacks an intact amino-terminal domain lying between the amino acids which precede amino acid residue 37 (cysteine) of the transdominant peptide sequence by between 10 and 50 amino acids; more preferably between 16 and 40, most preferably between 16 and 36. Alternatively, or additionally, the transdominant peptide sequence lacks an intact cysteine-rich domain lying within the amino acid residues within 30 amino acid residues contiguous to and preceding the transdominant peptide sequence (e.g., amino acid residue 37). Preferably, a cysteine-rich domain is absent within the 20 amino acids contiguous to residue 37 of the transdominant peptide sequence. More preferably, a cysteine-rich domain is absent within the 16 amino acids contiguous to residue 37 of the transdominant peptide sequence. Most preferably, the cysteine-rich domain does not overlap the transdominant peptide sequence at amino acid 37 or reside within the preceding 15 contiguous amino acids from amino acid 37.

The presence of an amino-terminal domain or a cysteine-rich domain can be identified using expression cassettes in which all of the up to 70 amino acids contiguous and proximal to amino acid residue 36 (inclusive) of the transdominant soluble Tat peptide are fused to amino acids 37 to 86 of a wild-type HIV-1 Tat protein. Transfection and CAT assays for transactivation of the HIV-1 LTR can be determined using methods known to those of skill in the art and as disclosed herein at Example 1. See, also, Kashanchi et al., *J. Virol,* 68(5):3298–3307 (1994); Pearson et al., *Proc. Natl. Acad. Sci. USA,* 87:5079–5083 (1990); Frankel et al., *Proc. Natl Acad. Sci. USA* 86:7397–7401 (1989). The fusion protein which lacks either an amino-terminal domain, a cysteine-rich domain, or both, will transactivate the HIV-LTR by less than 20% relative to the wild-type HIV-1 Tat protein control, preferably by less than 15%, more preferably by less than 10%, and most preferably by less than 5%.

Nucleic Acids Encoding Transdominant Soluble Tat Peptides

The present invention provides isolated nucleic acids encoding each of the transdominant soluble Tat peptides of the present invention as described more fully, supra.

The isolated nucleic acids encoding transdominant soluble Tat peptides can be RNA, DNA, or chimeras thereof.

Nucleic acids encoding transdominant soluble Tat peptides can be made using standard recombinant or synthetic techniques. With the amino acid sequences of the transdominant soluble Tat peptides herein provided, one of skill can readily construct a variety of clones containing functionally equivalent nucleic acids, such as nucleic acids which differ in sequence but which encode the same peptides. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Sambrook, et al., *Molecular Cloning: A Laboratory Manual* (2nd Ed., Vols. 1–3, Cold Spring Harbor Laboratory (1989)), *Methods in Enzymology*, Vol. 152: *Guide to Molecular Cloning Techniques* (Berger and Kimmel (eds.), San Diego. Academic Press, Inc. (1987)), or *Current Protocols in Molecular Biology*, (Ausubel, et al. (eds.), Greene Publishing and Wiley-Interscience, New York (1987). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The isolated nucleic acid compositions of this invention can also be synthesized in vitro. Deoxynucleotides can be synthesized chemically according to the solid phase phosphoramidite triester method described by Beaucage and Caruthers (1981), *Tetrahedron Letts.*, 22(20):1859–1862, e.g., using an automated synthesizer, e.g., as described in Needham-VanDevanter et al. (1984) *Nucleic Acids Res.*, 12:6159–6168.

Expression of Nucleic Acids Encoding a Transdominant Soluble Tat Peptide

Once the isolated nucleic acids encoding an transdominant soluble Tat peptide of the present invention are constructed, one can express them in a recombinantly engineered cell such as bacteria, yeast, insect (especially employing baculoviral vectors), and mammalian cells. A "recombinant protein" is a protein produced using cells that do not have an endogenous copy of the DNA construct (e.g., a vector) which is able to express the protein. The cells produce the recombinant protein because they have been genetically altered by the introduction of the appropriate nucleic acid sequence.

It is expected that those of skill in the art are knowledgeable in the numerous expression systems available for expression of DNA encoding transdominant soluble Tat peptides. No attempt to describe in detail the various methods known for the expression of proteins in prokaryotes or eukaryotes will be made.

In brief summary, the expression of nucleic acids encoding transdominant soluble Tat peptides will typically be achieved by operably linking the DNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the transdominant soluble Tat peptide. To obtain high level expression of a cloned gene, it is desirable to construct expression vectors which contain, at the minimum, a strong promoter to direct transcription, a ribosome binding site for translational initiation, and a transcription/translation terminator. Methods of expression in prokaryotes or eukaryotes are disclosed in, for example, Sambrook et al., Berger and Kimmel, and Ausubel et al., all supra.

The transdominant soluble Tat peptides of this invention, recombinant or synthetic, can be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982); Deutscher, Guide to Protein Purification, Academic Press, 1990. For example, antibodies may be raised to the transdominant soluble Tat peptides as described herein. The protein may then be isolated from cells expressing the recombinant transdominant soluble Tat peptide and further purified by standard protein chemistry techniques.

Methods of Inhibiting HIV Replication

The present invention also provides methods of inhibiting HIV transcription or translation (i.e., HIV replication) in a mammalian cell, most preferably a primate cell such as macaques, chimpanzees, or human cells. The method comprises administering to a mammalian cell a therapeutically effective amount of a transdominant soluble Tat peptide of the present invention, wherein the therapeutically effective amount is sufficient to inhibit HIV replication. Administration of the transdominant soluble Tat peptide may be accomplished by administering the peptide itself to a mammalian cell, or by expression from a nucleic acid encoding a transdominant soluble Tat peptide of the present invention. Typically, the replication of HIV is inhibited by at least 20%, in some embodiments by at least 30%, more often at least 40%, generally, at least 50%, preferably at least 60%, more preferably at least 70%, and most preferably at least 80%. Preferably, the viral strain whose replication is inhibited is HIV-1, HIV-2, or SIV. Methods of assessing inhibition of HIV or SIV replication are known to those of ordinary skill in the art. See, e.g., Example 3; and, Kashanchi et al, *J. Virol.*, 68(5):3298–3307 (1994).

A. Pharmaceutical Compositions

The transdominant soluble Tat peptides of the present invention can be administered by provision of the transdominant soluble Tat peptide itself, or by expression of a nucleic acid which encodes a transdominant soluble Tat peptide. Generally, a therapeutically effective amount of the transdominant Tat peptide is administered under physiological conditions. Physiological conditions are those which support cell viability and biosynthesis. Typically, physiological conditions also support the proliferation of cells. Thus, the term "physiological conditions" includes reference to conditions (e.g., temperature, osmolarity, pH) that are typical inside a living organism or a cell. While it is recognized that some organs are subject to extreme conditions, the intra-organismal and intra-cellular environment normally varies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The transdominant soluble Tat peptides of the present invention, and nucleic acids encoding the transdominant soluble Tat peptides of the present invention are useful for parenteral, intravenous, topical, oral, or local administration, such as by aerosol or transdermally, for prophylactic and/or therapeutic treatment of a mammal, particularly a human. The pharmaceutical compositions can be administered in a variety of unit dosage forms depending upon the method of administration.

The compositions containing the present transdominant soluble Tat peptides (or nucleic acids encoding them) can be administered for therapeutic or prophylactic treatments. In therapeutic applications, compositions are administered to a patient suffering from an HIV infection in an amount sufficient to at least partially arrest the disease and its complications. In prophylactic application, compositions are administered to a patient susceptible to an HIV infection in an amount sufficient to at least inhibit transcription from the HIV LTR, or inhibit translation of a TAR mRNA. An amount adequate to accomplish this is defined as a "therapeutically effective dose." Amounts effective for this use will depend upon the severity of the disease and the general state of the patient's health. Means of assessing inhibition of HIV replication, transcription, and translation are known to those of skill in the art, and discussed, supra.

Single or multiple administrations of the compositions may be administered depending on the dosage and frequency as required and tolerated by the patient. In any event, the composition should provide a sufficient quantity of the peptides or nucleic acids of this invention to effectively treat the patient.

Formulations suitable for oral administration can consist of (a) liquid solutions, such as an effective amount of the packaged nucleic acid suspended in diluents, such as water, saline or PEG 400; (b.) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

Peptide or nucleic acid compositions of the invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of nucleic acids or peptides of the invention can be presented in unit-dose or multi-dose sealed containers, such as ampules and vials.

Injection solutions and suspensions can be prepared from sterile powders, granules, and tablets of the kind previously described. Cells transfected by the nucleic acid as described in the context of ex vivo therapy can also be administered intravenously or parenterally as described infra. Actual methods for preparing parenterally administrable compositions will be known or apparent to those skilled in the art and are described in more detail in such publications as *Remington's Pharmaceutical Science,* 19th ed., Mack Publishing Company, Easton, Pa. (1995).

B. Administration of Transdominant Soluble Tat Peptides

Methods of introducing peptides into cells are well known in the art. It is recognized that the transdominant soluble Tat peptides when administered orally, must be protected from digestion. This is typically accomplished either by complexing the peptide with a composition to render it resistant to acidic and enzymatic hydrolysis or by packaging the peptide in an appropriately resistant carrier such as a liposome. Means of protecting proteins from digestion are well known in the art.

For example, numerous emulsion based systems have been proposed as pharmaceutical formulations for administration of peptides and proteins. In most cases, those emulsions may be characterized as water-in-oil microemulsions, which are thermodynamically stable and usually self-emulsifying; see Cho et al., WO 90/03164; Cho et al., WO 91/14454; Affinity, WO 92/18147; Riley, U.S. Pat. No. 5,055,303; Ritschel, Meth. Find. Exp. Clin. Pharmacol. 13:205–220 (1991). In each of these cases, the internal dispersed phase containing the protein typically is aqueous and the continuous phase typically is lipoidal. Other emulsions have been disclosed in the submicron size range which contain specific ingredients such as lysophosphatidylcholine (Yesair, WO 92/03121).

Zerbe et al., WO 93/00076, disclose a drug delivery system consisting of a suspension of microparticles having a spherical core composed of a biopolymer, preferably a protein such as albumin or gelatin, which typically has been crosslinked or denatured to maintain its structural coherency. The spherical core can be combined with a bioadhesive polymer. Riley, U.S. Pat. No. 5,055,303, discloses a bioadherent emulsion of the water-in-hydrophobic phase type, wherein the continuous hydrophobic phase is a solid fat. U.S. Pat. No. 5,514,670 discloses emulsions which include submicron particles, a peptide, and an aqueous continuous phase that enhances oral bioavailability of the peptide. The aqueous continuous phase promotes absorption of the bioactive peptide through mucosal surfaces by achieving mucoadhesion of the emulsion particles.

Other types of microparticulate drug delivery systems also have been proposed as suitable for oral administration of therapeutic proteins, such as microspheres (WO 93/00077), lipospheres (Domb, U.S. Pat. No. 5,188,837), microcapsules (EP 442671), liposomes (WO 91/05545), or other lipid vesicles (Yoshida et al., EP 140,085). See, also, WO 90/03164; WO 91/14454; WO 92/18147; U.S. Pat. Nos. 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

In preferred embodiments, the transdominant peptide sequence of the present invention is linked to a targeting ligand which provides selective binding to a desired cell receptor or allows transport into an anatomical site. Targeting ligands selective for T-cells are known in the art.

Callebaut et al. (*Virology,* 218:181–192 (1996), incorporated herein by reference) teach template assembled synthetic peptides (TASP) in which a lysine-rich short peptide (KKKGPKEKGC (SEQ ID NO:10) or KKKKKGC (SEQ ID NO:11) was used as a template to covalently anchor arrays of tripeptides, such as RPR, RPK, or KPR, at the ε-amino groups of the lysine residues in the templates using Boc and Fmoc solid-phase methodology. The RP dipeptide present in these arrays is a highly conserved motif in the V3 loop of the extracellular envelope glycoprotein of different types of HIV isolates. This extracellular glycoprotein contains the binding site for the CD4 receptor. Pentavalent presentation of 5(RPR)-(SEQ ID NO:12) 5(RPK)-(SEQ ID NO:13), or 5(KPR)-(SEQ ID NO:14) TASP molecules were strongly inhibitory for HIV infection.

A transdominant peptide sequence of the present invention can be linked internally, or at the amino or carboxy terminal end of one or more of the peptides in these pentavalent TASP structures to provide targeting to T-cells. In particularly preferred embodiments, one or more amino acids in the TASP molecule and/or in the transdominant peptide sequence are D-amino acid analogs. Additionally, reduced peptide bond analogs between the amino terminal and penultimate amino terminal amino acids of the TASP peptides and/or the transdominant soluble Tat peptide can be used to increase the anti-viral potency of the TASP-transdominant soluble Tat peptide conjugate. Reduced peptide bond analogs are known in the art and can be synthesized by reductive amination of N-Boc-α-amioaldehydes in dimethylformamide containing 1% acetic acid. Sasaki and Coy, *Peptides,* 8:119–121 (1987); Guichard et al., *Pept. Res.,* 6:121–124 (1993), both of which are incorporated herein by reference. Linkage via peptide bonds or chemical crosslinkers is known in the art. Linker molecules are readily available from commercial sources (Pierce Chemical Company, Rockford Ill.).

A "linker", as used herein, is a molecule that is used to join two molecules. The linker is capable of forming covalent bonds to both molecules.

Suitable linkers are well known to those of skill in the art and include, but are not limited to, straight or branched-chain carbon linkers, heterocyclic carbon linkers, or peptide linkers. Where both molecules are polypeptides, the linkers may be joined to the constituent amino acids through their side groups (e.g., through a disulfide linkage to cysteine).

Many procedures and linker molecules for attachment of various compounds including radionuclide metal chelates, toxins and drugs to proteins are known. See, for example, .European Patent Application No. 188,256; U.S. Pat. Nos. 4,671,958, 4,659,839, 4,414,148, 4,699,784; 4,680,338; 4,569,789; 4,589,071; and Borlinghaus et al. *Cancer Res.* 47: 4071–4075 (1987), which are incorporated herein by reference.

In some circumstances, it is desirable to free the peptide of the present invention from the ligand when the chimeric molecule has reached its target site. Therefore, chimeric conjugates comprising linkages which are cleavable in the vicinity of the target site may be used when the effector is to be released at the target site. Cleaving of the linkage to release the agent from the ligand may be prompted by enzymatic activity or conditions to which the immunoconjugate is subjected either inside the target cell or in the vicinity of the target site.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies, one skilled in the art will be able to determine a suitable method for attaching a given agent to an antibody or other protein.

In other embodiments, a transdominant peptide sequence of the present invention is linked to a synthetic polymeric construct (SPC) which includes the consensus sequence of the HIV-1 surface envelope glycoprotein gp120 V3 loop (GPGRAF (SEQ ID NO.15)). See, Yahi et al., *J. of Virology,* 68(9):5714–5720 (1994). The SPC is a multibranched structure constructed using standard solid-phase synthetic methods. Briefly, peptide chains are elongated stepwise on 4-(oxy-methyl)-phenylacetamidomethyl resins by using t-butyloxycarbonyl-benzyl chemistry. Sabatier et al., *Biochemistry,* 32:2763–2770 (1993). The SPC is constructed using multimeric V3 loop consensus sequences linked to amino groups of lysine residues. For example, [GPGRAF]$_8$-SPC is a multibranched structure comprising eight GPGRAF (SEQ ID NO:15) sequences, with each of the GRGRAF (SEQ ID NO:15) dsequences linked to an amine group of lysine (K) in the multimeric structure: $(K)_4$-$(K)_2$-$(K)$-$\beta A$. Multibranched (dendrimeric) structures are known in the art. The SPC typically includes at least six of the V3 loop consensus sequences, and preferably at least eight of the V3 loop consensus sequences, but less than 100 V3 loops, preferably less than 50, more preferably less than 25, and most preferably less than 15. The SPC may be linked to the transdominant peptide sequence at the carboxy terminal amino acid, amino terminal amino acid, or via an internal amino acid. Preferably, linkage is achieved via a peptide bond to the amino terminus of the transdominant peptide sequence.

The compositions for administration will commonly comprise a solution of the transdominant soluble Tat peptide dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg of peptide per patient per day. Dosages from 0.1 up to about 100 mg per patient per day may be used, particularly when the peptide composition is administered to a secluded site and not into the blood stream, such as into a body cavity or into a lumen of an organ. As will be readily understood by the clinician of ordinary skill in the art, the dose will be dependent upon the properties of the particular peptide employed, e.g., its activity and biological half-life, the concentration of peptide in the formulation, the site and rate of dosage, the clinical tolerance of the patient involved, the severity of the disease, and the like.

C. Administration of Nucleic Acids Encoding Transdominant Soluble Tat Pep tides

Cells can be transfected with a nucleic acid encoding a transdominant soluble Tat peptide of the present invention in vitro and in vivo. The term "transfected" includes reference to the introduction of a nucleic acid into a eukaryotic cell where the nucleic acid can be incorporated into the genome of the cell (i.e., chromosome, plasmid, or mitochondrial DNA), converted into an autonomous replicon, or transiently expressed (e.g., transfected mRNA).

A variety of methods for delivering and expressing a nucleic acid within a mammalian cell are known to those of ordinary skill in the art. Such methods include, for example liposome-based gene delivery (Debs and Zhu (1993) WO 93/24640; Mannino and Gould-Fogerite (1988) *Bio Techniques* 6(7): 682–691; Rose U.S. Pat No. 5,279,833; Brigham (1991) WO 91/06309; Felgner et al. (1987) *Proc. Natl. Acad. Sci. USA* 84: 7413–7414; and, Budker et al., *Nature Biotechnology*, 14(6):760–764 (1996)). Other methods known to the skilled artisan include electroporation (U.S. Pat. Nos. 5,545,130, 4,970,154, 5,098,843, and 5,128,257), direct gene transfer, cell fusion, precipitation methods, particle bombardment, and receptor-mediated uptake (U.S. Pat. Nos. 5,547,932, 5,525,503, 5,547,932, and 5,460,831). See also, U.S. Pat. No. 5,399,346.

Following transfection of a nucleic acid encoding a transdominant soluble Tat peptide, a therapeutically effective amount of the peptide is expressed. Such genetic therapy procedures have been used to correct acquired and inherited genetic defects, cancer, and viral infection in a number of contexts. The ability to express artificial nucleic acids in humans facilitates the prevention and/or cure of many important human diseases, including many diseases which are not amenable to treatment by other therapies. As an example, in vivo expression of cholesterol-regulating genes, genes which selectively block the replication of HIV, and tumor-suppressing genes in human patients dramatically improves the treatment of heart disease, AIDS, and cancer, respectively. For a review of gene therapy procedures, see Anderson, *Science* (1992) 256:808–813; Nabel and Felgner (1993) *TIBTECH* 11: 211–217; Mitani and Caskey (1993) *TIBTECH* 11: 162–166; Mulligan (1993) *Science* 926–932; Dillon (1993) *TIBTECH* 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al. (1995) in *Current Topics in Microbiology and Immunology* Doerfler and Böhm (eds) Springer-Verlag, Heidelberg Germany; and Yu et al., *Gene Therapy* (1994) 1:13–26.

In preferred embodiments, a nucleic acid encoding a transdominant soluble Tat peptide of the present invention is operably linked to a promoter which is preferentially induced in HIV infected cells. Accordingly, introduction and induction of this promoter-nucleic acid construct in HIV infected cells directs expression of the nucleic acid encoding a transdominant soluble Tat peptide. Preferred promoters include the $VA_1$ promoter (GenBank Accession No. M35961) from adenovirus, and the LTR promoter. The sequence of the $VA_1$ and LTR promoters are well known in the art and provided below.

$VA_1$ Promoter 1 gggcactctt ccgtggtctg gtggataaat tcgcaagggt atcatggcgt ggacgaccgg 61 ggttcgaacc ccggatccgt gatccatgcg gttaccgtcc gccgcccgtg cgtcgaaccc 121 aggtgtgcga cgtcagacaa cggggagcg ctcctt (SEQ ID NO:16).

LTR Promoter

TCGAGCTTGCTACAAGGGACTTTC-CGCTGGGGACTTTCCAGGGAGGCGTGGC-CTGGGCGGGACTGGGGAGTGGCGA GCCCTCAGAT-GCTGCATATAAGCAGCTGCTTTTTGCCTGTACTGG GTCTCTCTGGTTAGACCAGATCTGAGCCTGG AGACTCTCTGGCTAACTAGGGAAC-CCACTGCTTAAGCCTCAATAAAG (SEQ ID NO:17). See, e.g., *DNA Tumor Viruses*, 2nd edition, Part II, Cold Spring Harbor (1980), John Tooze (Ed.); Kashanchi et al., *J. of Virology*, 68(5):3298–3307 (1994), both of which are incorporated herein by reference.

Delivery of the gene or genetic material into the cell is the first critical step in gene therapy treatment of disease. A large number of delivery methods are well known to those of skill in the art. Such methods include, for example liposome-based gene delivery (Debs and Zhu (1993) WO 93/24640; Mannino and Gould-Fogerite (1988) *Bio Techniques* 6(7): 682–691; Rose U.S. Pat. No. 5,279,833; Brigham (1991) WO 91/06309; and Felger et al. (1987) *Proc. Natl. Acad. Sci. USA* 84: 7413–7414), and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4:43, and Cornetta et al. *Hum. Gene Ther.* 2:215 (1991)). Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al. (1992) *J. Virol.* 66(5) 2731–2739; Johann et al. (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra).

AAV-based vectors can be used to transfect cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) Human *Gene Therapy* 5:793–801; Muzyczka (1994) *J. Clin. Invst.* 94:1351 and Samulski (supra) for an overview of AAV vectors. Construction of recombinant AAV vectors are described in a number of publications, including Lebkowski, U.S. Pat. No. 5,173, 414; Tratschin et al. (1985) *Mol. Cell. Biol.* 5(11) :3251–3260; Tratschin, et al. (1984) Mol. Cell. Biol., 4:2072–2081; Hermonat and Muzyczka (1984) *Proc. Natl. Acad. Sci. USA,* 81:6466–6470; McLaughlin et al. (1988) and Samulski et al. (1989) *J. Virol.,* 63:03822–3828. Cell lines that can be transformed by rAAV include those described in Lebkowski et al. (1988) *Mol. Cell. Biol.,* 8:3988–3996.

1. Ex vivo Transfection of Cells

Ex vivo cell transfection for gene therapy (e.g., via re-infusion of the transformed cells into the host organism) is well known to those of skill in the art. In a preferred embodiment, cells are isolated from the subject organism, transfected with a nucleic acid encoding a transdominant soluble Tat peptide (alone or in a vector), and re-infused back into the subject organism (e.g., a human patient). Various cell types suitable for ex vivo transfection are well known to those of skill in the art (see, e.g., Freshney et al., *Culture of Animal Cells, a Manual of Basic Technique, Third edition* Wiley-Liss, New York (1994)) and the references cited therein for a discussion of how to isolate and culture cells from patients).

The nucleic acid encoding a transdominant soluble Tat peptide is placed in a vector under the control of an activated or constitutive promoter, or under the control of an inducible promoter. The transfected cell(s) express a therapeutically effective amount of the peptide to inhibit replication of HIV, or to inhibit transcription or translation of HIV nucleic acids.

In one particularly preferred embodiment, stem cells are used in ex-vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating $CD34^+$ cells in vitro into clinically important immune cell types using cytokines such a GM-CSF, IFN-γ and TNF-α are known (see, Inaba et al. (1992) *J. Exp. Med.* 176, 1693–1702, and Szabolcs et al. (1995) 154: 5851–5861).

Stem cells are isolated for transfection and differentiation using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as $CD4^+$ and $CD8^+$ (T cells), $CD45^+$ (panB cells), GR-1 (granulocytes), and $Ia^d$ (differentiated antigen presenting cells). For an example of this protocol see, Inaba et al. (1992) *J. Exp. Med.* 176, 1693–1702.

In humans, bone marrow aspirations from iliac crests are performed, e.g., under general anesthesia in the operating room. The bone marrow aspirations is approximately 1,000 ml in quantity and is collected from the posterior iliac bones and crests. If the total number of cells collected is less than about $2 \times 10^8$/kg, a second aspiration using the sternum and anterior iliac crests in addition to posterior crests is performed. During the operation, two units of irradiated packed red cells are administered to replace the volume of marrow taken by the aspiration. Human hematopoietic progenitor and stem cells are characterized by the presence of a CD34 surface membrane antigen. This antigen is used for purification, e.g., on affinity columns which bind CD34. After the bone marrow is harvested, the mononuclear cells are separated from the other components by means of ficol gradient centrifugation. This is performed by a semi-automated method using a cell separator (e.g., a Baxter Fenwal CS3000+ or Terumo machine). The light density cells, composed mostly of mononuclear cells are collected and the cells are incubated in plastic flasks at 37° C. for 1.5 hours. The adherent cells (monocytes, macrophages and B-Cells) are discarded. The non-adherent cells are then collected and incubated with a monoclonal anti-CD34 antibody (e.g., the murine antibody 9C5) at 4° C. for 30 minutes with gentle rotation. The final concentration for the anti-CD34 antibody is 10 μg/ml. After two washes, paramagnetic microspheres (Dyna Beads, supplied by Baxter Immunotherapy Group, Santa Ana, Calif.) coated with sheep anti-mouse IgG (Fc) antibody are added to the cell suspension at a ratio of 2 cells/bead. After a further incubation period of 30 minutes at 4° C., the rosetted cells with magnetic beads are collected with a magnet. Chymopapain (supplied by Baxter Immunotherapy Group, Santa Ana, Calif.) at a final concentration of 200 U/ml is added to release the beads from the CD34+ cells. Alternatively, and preferably, an affinity column isolation procedure can be used which binds to CD34, or to antibodies bound to CD34 (see, the examples below). See, Ho et al. (1995) *Stem Cells* 13 (suppl. 3): 100–105. See also, Brenner (1993) *Journal of Hematotherapy* 2: 7–17.

In another embodiment, hematopoietic stem cells are isolated from fetal cord blood. Yu et al. (1995) *Proc. Natl. Acad. Sci. USA,* 92: 699–703 describe a method of transfecting $CD34^+$cells from human fetal cord blood using retroviral vectors.

2. In vivo Transfection

Vectors (e.g., retroviruses, adenoviruses, liposomes, etc.) containing nucleic acids encoding a transdominant soluble Tat peptide can be administered directly to the organism for transfection of cells in vivo, or a nucleic acid of the present invention can be transfected directly (i.e., in the absence of a vector). Administration is by any of the routes normally used for introducing a molecule into ultimate contact with blood or tissue cells. The nucleic acids are administered in any suitable manner, preferably with pharmaceutically acceptable carriers. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention as discussed supra.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transfected cell type in a particular patient.

In determining the effective amount of the vector to be administered in the treatment or prophylaxis of conditions owing to HIV infection, the physician evaluates circulating plasma levels of the vector, vector toxicities, progression of the disease, and the production of anti-vector antibodies. In general, the dose equivalent of a naked nucleic acid from a vector (if employed) is from about 1 μg to 100 μg for a typical 70 kilogram patient, and doses of vectors which include a retroviral particle are calculated to yield an equivalent amount of therapeutic nucleic acid.

For administration, inhibitors and transfected cells of the present invention can be administered at a rate determined by the LD-50 of the inhibitor, vector, or transfected cell type, and the side-effects of the inhibitor, vector or cell type at various concentrations, as applied to the mass and overall health of the patient. Administration can be accomplished via single or divided doses.

In a preferred embodiment, prior to infusion, blood samples are obtained and saved for analysis. Between $1\times10^8$ and $1\times10^{12}$ transfected cells are infused intravenously over 60–200 minutes. Vital signs and oxygen saturation by pulse oximetry are closely monitored. Blood samples are obtained 5 minutes and 1 hour following infusion and saved for subsequent analysis. Leukopheresis, transfection and reinfusion can be repeated are repeated every 2 to 3 months. After the first treatment, infusions can be performed on a out-patient basis at the discretion of the clinician. If the reinfusion is given as an outpatient, the participant is monitored for at least 4, and preferably 8 hours following the therapy.

Transfected cells are prepared for reinfusion according to established methods. See, Abrahamsen et al. (1991) *J. Clin. Apheresis,* 6: 48–53; Carter et al. (1988) *J. Clin. Arpheresis,* 4:113–117; Aebersold et al. (1988) *J. Immunol. Meth.,* 112: 1–7; Muul et al. (1987) *J. Immunol. Methods,* 101:171–181 and Carter et al. (1 987) *Transfusion* 27: 362–365. After a period of about 2–4 weeks in culture, the cells should number between $1\times10^8$ and $1\times10^{12}$. In this regard, the growth characteristics of cells vary from patient to patient and from cell type to cell type. About 72 hours prior to reinfusion of the transfected cells, an aliquot is taken for analysis of phenotype, and percentage of cells expressing the transdominant soluble Tat peptide.

Although the present invention has been described in some detail by way of illustration and example for purposes of clarity of understanding, it will be obvious that certain changes and modifications can be practiced within the scope of the appended claims.

EXAMPLE 1

Example 1 describes the suppression of transcriptional transactivation using soluble Tat peptides.

Initial studies focused on the analysis of a series of Tat peptide analogs, containing various amino acid substitutions, for their ability to inhibit Tat transactivation of the HIV-1 promoter. CEM lymphocytes, grown to early- to mid-log phase, were electroporated with the Tat protein (1 μg), Tat core peptide 36–50 (5 μg) and the HIV-1 LTR-CAT reporter (5 μg).

The amino acid sequence for the Tat peptides are:

Tat 36–50: V-C-F-T-T-K-A-L-G-I-S-Y-G-R-K (SEQ ID NO:2)

Tat 36–50 (41): V-C-F-T-T-A-A-L-G-I-S-Y-G-R-K (SEQ ID NO:3)

Tat 36–50 (44): V-C-F-T-T-K-A-L-S-I-S-Y-G-R-K (SEQ ID NO:4)

Tat 36–50 (46): V-C-F-T-T-K-A-L-G-I-A-Y-G-R-K (SEQ ID NO:5)

Tat 36–50 (47): V-C-F-T-T-K-A-L-G-I-S-A-Y-G-R-K (SEQ ID NO:6)

Tat 36–50 (41/44): V-C-F-T-T-A-A-L-A-I-S-Y-G-R-K (SEQ ID NO:7)

Tat 36–50 (41/46): V-C-F-T-T-A-A-L-G-I-A-Y-G-R-K (SEQ ID NO:8)

Tat 36–50 (41/47): V-C-F-T-T-A-A-L-G-I-S-A-G-R-K (SEQ ID NO:9).

Cells were electroporated as described previously (Kashanchi F, et al. (1992), *Nucleic Acids Res,* 20:4673–4674). CEM CD4+ lymphocytes (12D7) (as well as U1 and HeLa cells described in subsequent examples) were kept at a density of 0.5 to $0.8\times10^6$ cells/ml with media added daily. Typically, $5\times10^6$ cells were electroporated with purified peptides, Tat protein and/or 5 μg of a reporter plasmid. Synthetic Tat peptides were purified by HPLC to 95 percent purity (Peptide Technologies Corporation, Gaithersburg, Md.). All peptides were analyzed for purity on a 4–20 percent gradient SDS/PAGE followed by silver staining. Recombinant Tat protein was purified by reverse phase HPLC and tested for functional activity in an in vitro transcription assay and in vivo electroporation into CEM cells (Kashanchi F, et al. (1992), *Nucleic Acids Res,* 20:4673–4674; Bohan Calif., et al. (1992) *Gene Expr,* 2:391–407). Tat peptide, Tat protein, and the reporter HIV LTR-CAT were mixed with cells and electroporated using a cell porater apparatus (Gibco/BRL, Gaithersburg, Md.). Cell mixtures were electroporated at 800 μF, 230 volts, in RPMI 1640 media without fetal calf serum. Following electroporation, cells were plated in 10 ml of complete media and samples collected 48 hours later for either CAT assay, p24 Gag antigen capture assay or northern blot analysis. Samples receiving rTNF-α (R & D System, Minneapolis, MN) after electroporation were collected 48 hours post-treatment for p24 Gag antigen capture assay (ABI, Bethesda, Md.).

Tat protein increased HIV-1 LTR-directed gene expression from 2.1 to 95 percent (45-fold). When wild type 36–50 peptide was included in the transfection no apparent drop in transcription activity was observed. This lack of competition between wild type Tat protein and wild type Tat peptide was also apparent when using each of the four single Tat peptide analogs, i.e. Tat 41, 44, 46, and 47 (each providing less than a 5% decrease in activity). In contrast, the Tat peptide analogs with double amino acid substitutions showed varying degrees of ability to inhibit HIV transfection. Most notably, peptide analog 41/44 showed suppression of Tat transactivation from 95.7 to 1.1 percent, peptide 41/46 showed suppression from 95.7% to 5.5%, and 41/47 showed suppression from 95.7% to 12%. Thus, in transient transfection assays, Tat peptide analogs were effective competitors for wild type Tat protein in downregulating Tat activated transcription.

In a separate experiment, the inhibitory activity of the short peptide 36–50 analogs were compared to longer derivatives containing amino acids 36–72. Both short and long peptide analogs containing double amino acid substitutions were more efficient inhibitors than those peptide analogs containing single amino acid substitutions. Interestingly, it is demonstrated below the short peptide analogs are more efficient at inhibiting Tat induced HIV-1 virus replication.

EXAMPLE 2

Example 2 describes the effect of Tat peptide analogs on other promoters.

It was of interest to determine if the peptides inhibited transcription from other polymerase II promoters. We have tested seven promoters including HTLV-1, CMV, PTHrP, IgH, RAS, RSV, and SIV. Each promoter, cloned upstream of the CAT reporter gene, was cotransfected individually with the Tat peptides under identical conditions. Electroporation was as in Example 1 but reporter genes used were HTLV-1 LTR (pU3R CAT, 5 μg) or pCMV-CAT (5 μg), containing the CMV promoter. Each of the independent experiments gave similar results; minimal inhibition was observed using the peptide analog 41/44. For example, basal transcription of the HTLV-1 promoter decreased from 19 to 15.6 and 16.4 percent using 1 and 5 μg of the peptide analog 41/44. Similarly, Tat peptide analog 41/44 decreased $Tax_1$ (1 μg) transactivated transcription approximately two-fold (49.2 to 22.8 percent). In other control experiments, transcription from the CMV promoter was decreased from 17.8 to 9.04 and 6.7 percent in the presence of 1 or 5 µg of Tat peptide analog 41/44. These results suggest that the Tat peptide analog 41/44 has an inhibitory effect on HIV-1 transactivation.

EXAMPLE 3

Example 3 describes the inhibition of viral replication by a Tat peptide analog in latently infected cells induced by Tat or TNF-α.

The ability of the Tat peptide analog 41/44 to inhibit HIV virus replication was tested in U1 cells, transfected as described in Example 1 with varying amounts of Tat protein. Supernatants were collected 48 hours later for p24 antigen capture assay. The U1 cells contained two integrated copies of the wild type HIV viral genome, but required either exogenous Tat or cytokines to produce viral particles. In the assays, maximum virus production was induced when approximately 2.5 to 5 µg of Tat protein was added to the cell culture. Consistent with the results obtained above, in comparison to the wild type peptide (5 µg), Tat peptide analog 41/44 (5 µg) inhibited Tat-induced virus production in U1 cells by approximately 85% when electroporated with 2.5 µg of Tat protein.

In a comparable experiment, the ability of Tat peptide analogs 36–72 to inhibit virus replication in Ul cells was tested. The addition of Tat protein (2.5 µg) to the U1 cells induced HIV-1 viral replication. The addition of peptide 36–72 failed to inhibit virus replication. Peptide analog 36–72 (41/44) inhibited virus replication by approximately 30%. Peptide analog 36–50 41/44 inhibited replication by approximately 75%. From these and other studies, it can be concluded that the short peptide analogs are more effective inhibitors of HIV-1 virus replication in U1 cells. Moreover, the double amino acid analogs are more effective inhibitors of transcription and virus replication than single amino acid analogs. In contrast to earlier studies of Green M, et al. (1989), *Cell*, 58:215–223, peptides alone, in the absence of Tat protein, did not induce viral replication in $U_1$ cells.

The cytokine TNF-α is also able to induce virus production in U1 cells (Chowdhury Ml, et al. (1993), *Virology*, 194:345–349; Huang L M, et al. (1994), *EMBO*, 13:2886–2896). In our assay conditions, the addition of 500 units of TNF-$^α$ to the growth media is sufficient to induce maximum virus production as judged by a HIV-1 p24 Gag antigen capture assay. Upon transfection of Tat peptide analog along with addition of TNF-α, we observed that the peptides decreased virus production by approximately 63%. Therefore, Tat peptide analogs are able to inhibit cytokine-induced HIV-1 replication. The level of inhibition is likely underestimated, since TNF-α will induce viral replication in a large percentage of cells. Conversely, the electroporated Tat peptide is most likely present in a small percentage of cells.

EXAMPLE 4

Example 4 describes the effect of Tat analog peptides in a co-cultivation assay.

It was of interest to determine whether the level of virus particles produced in the presence of Tat peptide analog 41/44 was sufficient to initiate a second round of virus replication. This is an important point to consider when designing specific inhibitors for HIV, since detection of p24 or reverse transcriptase in particles is not necessarily an indication of infectious particles. Dimitrov and Martin, *Nature*, 375:194–195 (1994). To address this question, we utilized co-cultivation assays in which the induced Ul cells were co-cultivated with the parental U937 monocyte cell line.

Transfected U1 cells ($5 \times 10^6$) were co-cultivated with the U937 cells 48 hrs after transfection. The co-cultivation assay was initially tested using either a 1:1, 1:5, or 1:25 ratio of infected to uninfected cells. A 1:5 co-cultivation was determined to be the optimal ratio in obtaining the highest viral production within a 2 week period. Cells were co-cultivated in a total of 4 mls for a period of 2 weeks. After the fist week, 2 mls of media cells was removed and 2 mls of fresh media added. Both U937 and CEM cells were seeded at a density of $0.5 \times 10^6$ cells per culture dish prior to the co-cultivation experiment.

Initially, cells were electroporated with either wild type (2.5 µg) or peptide analog 41/44 (2.5 µg), along with Tat protein. The p24 antigen capture assays were performed 48 hrs posttransfection on 400 µl aliquots of the infected culture; the remaining cells were used for co-cultivation assays. The results of this experiment demonstrated that the initial inhibition of HIV-1 virus production by the peptide analog 41/44, was sufficient to inhibit subsequent rounds of virus replication in the co-cultivation assay. Following seven days of co-cultivation, virus production was decreased by 85%. Consistent with the transfection assay data, the wild type core peptide did not inhibit HIV virus replication. Peptides alone, in the absence of Tat protein, did not induce viral replication. In an independent analysis, we have also examined a co-cultivation of $U_1$ with CEM $CD4^+$ T-lymphocytes and observed a similar result with the peptide analog 41/44 after 14 days of co-cultivation.

Importantly, no toxic effect of the peptides was observed in the cell culture assays. Microscopic inspection and trypan blue staining revealed no significant difference between control and experimental cultures. As a further control, the effect of the peptides were also monitored at the mRNA expression level using northern blots.

For northern blot analysis, U1 or HLM1 (Tat HIV proviral clone, Sadaie M R, et al. (1994), *Virology*, 202:513–518) cells were transfected with either Tat protein, or Tat protein in combination with peptides and collected 48 hrs later. Total RNA was extracted using the Trizol reagent (Gibco/BRL). RNA concentration was measured and equivalent amounts of RNA (5 µg) were loaded on a formaldehyde-agarose gel. The RNA was blotted onto nitrocellulose and hybridized with a randomly primed $^{32}$P-labelled HIV-1 proviral genome BH10 (Lofstrand, Inc.), histone H2b, β-Actin or GAPDH probe (Oncor Science, Inc.). Blots were washed, exposed and quantitated using a PhosphorImager (Molecular Dynamics) spectrophotometer.

Cellular RNAs including actin, histone H2b, and GAPDH, were monitored in cells treated with Tat and peptide analogs. Consistent with the results of the p24 virus replication assays in U1 cells treated with Tat and the 41/44 Tat peptide analog, a decrease in the level of HIV-1 viral mRNA was detected. In contrast, no change in the expression of the cellular GAPDH gene was observed.

In a separate experiment, a longer version of the 41/44 peptide analog was introduced into HeLa HLM1 cells. These cells contain a triple termination codon in the Tat gene, but otherwise contain wild type HIV-1 sequence. Similar to the results observed in the U1 cells, a significant decrease in viral mRNA (90% of full length mRNA) was observed in the cells treated with the Tat peptide. In contrast, no change in the levels of H2b, β-actin or GAPDH mRNA were detected.

These results suggest that the Tat peptide analogs selectively inhibit HIV-1 virus mRNA synthesis and are not toxic to these cells.

EXAMPLE 5

Example 5 describes the inhibition of Tat Binding Protein (TBP) directed transcription of the HIV-1 promoter by the Tat peptide.

It was of interest to determine if the Tat peptide analog targeted the interaction of Tat with TBP in vivo. For these experiments, we used a minimal HIV-1 promoter (−31 to +21) with Gal4 binding sites located upstream of the promoter. CEM cells were transfected with combinations of Gal4-TATA$^+$/TAR$^-$ reporter plasmid, Gal4-Tat and a CMV-TBP expression plasmid. Southgate CD, et al. (1991), *Genes Dev,* 5:2496–2507; Horikoshi N, et al. (1995), *Mol Cell Biol,* 15:227–234. Peptides were added at the time of electroporation. Following electroporation, cells were plated in complete media, harvested at 48 hours and CAT assays performed. The Gal4-TAT$^+$/TAR$^-$ plasmid contains six Gal4 binding sites, followed by the HIV sequence from −31 to +25. This construct contains no Sp1 sites or a TAR element.

The ability of Gal4-Tat to activate this promoter is dependent upon the presence of exogenously added TBP. This is in agreement with recently published data, which demonstrates that TBP or TBP-containing complexes allow Tat transactivation from the HIV-1 promoter. Xhou Q, et al. (1995), *EMBO J,* 14:321–328; Huang L M, et al. (1994), *EMBO,* 13:2886–2896. We next examined if the peptides were capable of downregulating the TBP/Tat-activated transcription by electroporating CEM T-cells with either wild type or peptide 41/44. The 41/44 peptide inhibited TBP/Tat-activated transcription. This result is consistent with the hypothesis that peptide 41/44 inhibits the functional interaction of Tat and TBP.

All publications and patents mentioned in this specification are herein incorporated by reference into the specification to the same extent as if each individual publication or patent was specifically and individually indicated to be incorporated herein by reference.

What is claimed is:

1. An isolated transdominant soluble Tat peptide, comprising a transdominant peptide sequence having the sequence Cys-Phe-Xaa$_{39}$-Xaa$_{40}$-Xaa$_{41}$-Gly-Leu-Gly-Ile-Ser-Xaa$_{47}$-Gly-Xaa$_{49}$-Lys (SEQ ID NO:1), wherein Xaa$_{39}$ is an amino acid residue selected from the group consisting of: Leu, Met, Ile, Thr, Gln, and Val; Xaa$_{40}$ is an amino acid residue selected from the group consisting of: Thr, Arg, Lys, and Asn; Xaa$_{41}$ is an amino acid residue exclusive of Lys; Xaa$_{47}$ is an amino acid residue selected from the group consisting of: Tyr and His; Xaa$_{49}$ is an amino acid residues selected from the group consisting of: Arg and Lys;

wherein said peptide sequence comprises at least one amino acid residue substitution, which is an amino acid other than the wild type amino acid, at a position selected from the group consisting of: 44, 46, and 47, and wherein the amino acid substitution is an amino acid residue selected from the group consisting of: Gly, Ala, Val, Leu, Ile, Pro, Phe, Tyr, Trp, Cys, Met, Ser, Thr, Lys, Arg, His, Asp, Glu, Asn, and Gln; and wherein said transdominant soluble Tat peptide lacks an intact amino-terminal domain or an intact cysteine-rich domain.

2. A method of inhibiting human immunodeficiency virus (HIV) replication in a mammalian cell, said method comprising administering a therapeutically effective amount of a transdominant soluble Tat peptide to said mammalian cell, said Tat peptide comprising a transdominant peptide sequence having the sequence Cys-Phe-Xaa$_{39}$-Xaa$_{40}$-Xaa$_{41}$-Gly-Leu-Gly-Ile-Ser-Xaa$_{47}$-Gly-Xaa$_{49}$-Lys (SEQ ID NO:1), wherein Xaa$_{39}$ is an amino acid residue selected from the group consisting of: Leu, Met, Ile, Thr, Gln, and Val; Xaa$_{40}$ is an amino acid residue selected from the group consisting of: Thr, Arg, Lys, and Asn; Xaa$_{41}$ is an amino acid residue exclusive of Lys; Xaa$_{47}$ is an amino acid residue selected from the group consisting of: Tyr and His; Xaa$_{49}$ is an amino acid residues selected from the group consisting of: Arg and Lys;

wherein said peptide sequence comprises at least one amino acid residue substitution, which is an amino acid other than the wild type amino acid, at a position selected from the group consisting of: 44, 46, and 47, and wherein the amino acid substitution is an amino acid residue selected from the group consisting of: Gly, Ala, Val, Leu, Ile, Pro, Phe, Tyr, Trp, Cys, Met, Ser, Thr, Lys, Arg, His, Asp, Glu, Asn, and Gln; and wherein said transdominant soluble Tat peptide lacks an intact amino-terminal domain or an intact cysteine-rich domain;

thereby inhibiting HIV replication.

3. The method of claim 2, wherein said therapeutically effective amount is administered ex vivo.

4. The method of claim 2, wherein said therapeutically effective dose is administered in vivo.

5. The method of claim 2, wherein said mammalian cell is a human cell.

6. The isolated transdominant soluble Tat peptide of claim 1, wherein said transdominant peptide sequence is linked to a pentavalent template assembled synthetic peptide (TASP) or synthetic polymeric construct (SPC), wherein said TASP comprises tripeptides selected from the group consisting of RPR, RRK, and KPR, and wherein said SPC comprises the polypeptide sequence GPGRAF (SEQ ID NO:15).

7. The isolated transdominant soluble Tat peptide according to claim 1, wherein Gly at position 44 is substituted with an amino acid residue selected from the group consisting of: Ser and Ala; and Ser at position 46 is substituted with an amino acid residue selected from the group consisting of: Tyr and Ala.

8. The method according to claim 2, wherein Gly at position 44 is substituted with an amino acid residue selected from the group consisting of: Ser and Ala; and Ser at position 46 is substituted with an amino acid residue selected from the group consisting of: Tyr and Ala.

* * * * *